US012167935B2

(12) United States Patent
Carter et al.

(10) Patent No.: US 12,167,935 B2
(45) Date of Patent: Dec. 17, 2024

(54) ULTRASOUND SYSTEM FOR A VIRTUAL SONOGRAPHY TEAM

(71) Applicant: FUJIFILM SONOSITE, INC., Bothell, WA (US)

(72) Inventors: Anthony R. Carter, Brier, WA (US); Harald Fiedler, Mukilteo, WA (US); Craig Chamberlain, Seattle, WA (US); Saeed Aliakbari, Snohomish, WA (US); Christopher Howard, Seattle, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 198 days.

(21) Appl. No.: 17/830,060

(22) Filed: Jun. 1, 2022

(65) Prior Publication Data
US 2023/0389898 A1 Dec. 7, 2023

(51) Int. Cl.
*A61B 8/00* (2006.01)
*A61B 8/08* (2006.01)

(52) U.S. Cl.
CPC ............ *A61B 8/463* (2013.01); *A61B 8/5223* (2013.01); *A61B 8/5207* (2013.01)

(58) Field of Classification Search
CPC ......... A61B 5/0002; A61B 8/56; A61B 8/463; A61B 8/5223; A61B 8/5207; A61B 8/4427; A61B 8/4477; A61B 8/565
See application file for complete search history.

(56) References Cited

U.S. PATENT DOCUMENTS

| | | | |
|---|---|---|---|
| 6,475,146 B1 * | 11/2002 | Frelburger | A61B 8/56 600/437 |
| 2015/0035959 A1 * | 2/2015 | Amble | A61B 5/0077 348/74 |

(Continued)

FOREIGN PATENT DOCUMENTS

| | | | | |
|---|---|---|---|---|
| DK | 2887878 T3 * | 1/2015 | | A61B 8/00 |
| EP | 2829234 A2 * | 1/2015 | | A61B 8/14 |
| WO | WO-2019072827 A1 * | 4/2019 | | A61B 5/4325 |

OTHER PUBLICATIONS

Ultrasound telemedicine system supporting compression of pre-scan-converted data, Proc. SPIE 3976, Medical Imaging 2000: Image Display and Visualization, (Apr. 18, 2000); https://doi.org/10.1117/12.383059 (Year: 2000).*

*Primary Examiner* — Sanjay Cattungal
(74) *Attorney, Agent, or Firm* — Womble Bond Dickinson (US) LLP

(57) ABSTRACT

Systems and methods for a virtual sonography team are described. An ultrasound system includes an ultrasound scanner that is configured to generate ultrasound data based on reflections of ultrasound signals transmitted by the ultrasound scanner and communicate the ultrasound data over a communication network to at least one display device and an archiver. An ultrasound machine is coupled to the ultrasound scanner and is configured to determine examination data for the ultrasound examination and communicate the examination data to the archiver over the communication network. The display device is configured to generate an ultrasound image based on the ultrasound data as part of an ultrasound examination and communicate the ultrasound image to the archiver for aggregation with the examination data into a patient record of the ultrasound examination.

21 Claims, 11 Drawing Sheets

(56) References Cited

U.S. PATENT DOCUMENTS

| | | | |
|---|---|---|---|
| 2019/0269384 A1* | 9/2019 | Lundberg | A61B 8/5207 |
| 2021/0345939 A1* | 11/2021 | Jumbe | A61B 5/0002 |
| 2022/0256227 A1* | 8/2022 | Rezazadegan Tavakoli | H04N 19/70 |
| 2023/0165562 A1* | 6/2023 | Sonnenschein | A61B 8/461 600/446 |

* cited by examiner

400

Generate, by an ultrasound scanner, ultrasound data based on reflections of ultrasound signals transmitted by the ultrasound scanner and communicate, over a communication network, the ultrasound data to at least one display device and an archiver ~/ 401

Determine, by an ultrasound machine, examination data for the ultrasound examination and communicate, over the communication network, the examination data to the archiver ~/ 402

Generate, by the at least one display device, an ultrasound image based on the ultrasound data as part of the ultrasound examination and communicate the ultrasound image to the archiver for aggregation with the examination data into a patient record of the ultrasound examination ~/ 403

| Generate, by an ultrasound scanner, ultrasound data based on reflections of ultrasound signals transmitted by the ultrasound scanner and communicate, over a communication network, the ultrasound data to a display device and an archiver | 501 |

| Generate, with a neural network implemented at least partially in hardware of the display device, an inference based on the ultrasound data and communicate the inference, over the communication network, to the archiver for aggregation with the ultrasound data into a patient record of the ultrasound examination | 502 |

| Communicate, by the archiver, the patient record, over the communication network, to a database of a care facility where the ultrasound examination is performed | 503 |

| Generate, by an ultrasound scanner, ultrasound data based on reflections of ultrasound signals transmitted by the ultrasound scanner and communicate, over a communication network, the ultrasound data to at least one display device and an archiver | 801 |

| Determine, by an ultrasound machine, examination data for the ultrasound examination and communicate, over the communication network, the examination data to the archiver | 802 |

| Generate, by the at least one display device, an ultrasound image based on the ultrasound data as part of the ultrasound examination and communicate the ultrasound image to the archiver for aggregation with the examination data into a patient record of the ultrasound examination | 803 |

| Generate, by an additional ultrasound scanner, additional ultrasound data based on additional reflections of additional ultrasound signals transmitted by the additional ultrasound scanner and communicate, over the communication network, the additional ultrasound data to at least one display device and the archiver | 804 |

| Generate, by the at least one display device, an additional ultrasound image based on the additional ultrasound data | 805 |

| Implement a neural network to generate, based on the ultrasound image and the additional ultrasound image, at least one of a label, a classification, a segmentation, a probability, and a new ultrasound image | 806 |

| Communicate, by the at least one display device, over the communication network and to the archiver, the at least one of the label, the classification, the segmentation, the probability, and the new ultrasound image for aggregation into the patient record | 807 |

FIG. 8

ULTRASOUND SYSTEM FOR A VIRTUAL SONOGRAPHY TEAM

FIELD

Embodiments disclosed herein relate to ultrasound systems. More specifically, embodiments disclosed herein relate to a virtual sonography team.

BACKGROUND

Ultrasound systems can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and can provide immediate imaging results without delay, ultrasound systems are often used at a point of care facility, such as in an emergency room. However, emergency rooms are usually crowded with equipment and staff (e.g., nurses, doctors, etc.), so that visibility of the ultrasound images is generally limited. For instance, usually only the operator of the ultrasound system (e.g., the sonographer) has an unencumbered view of the ultrasound images on the display screen of the ultrasound system; other staff are generally not able to adequately see the clinical display screen. This problem is often exacerbated by the small screen size of many ultrasound systems, which can be of a hand-held form factor, and the limitation that most ultrasound systems include a single, clinical display. Moreover, due to security concerns, many care facilities do not permit data from the ultrasound systems to be transmitted outside of the care facility's in-house network, which prevents remote assistance via an Internet connection. Consequently, most ultrasound systems are constrained to the single, clinical display for viewing ultrasound images, and it is the exclusive duty of the sonographer to operate the ultrasound system.

However, the sonographer is usually responsible for performing a significant number of duties related to operating the ultrasound system. For example, modern ultrasound systems usually include numerous adjustments for imaging parameters that can be made by the sonographer. In some cases, the ultrasound systems include sophisticated signal processing algorithms, such as artificial intelligence (AI), machine learning, and neural network implementations, which can be manually enabled by the sonographer. Additionally, the sonographer can be responsible for annotating ultrasound images, recording biometric data for the patient, saving/archiving ultrasound images, and the like. Because of the numerous responsibilities required of the sonographer, the sonographer is sometimes not capable of performing all the duties, and/or is sometimes forced to make a timely decision based on incomplete data. Consequently, the patient may not receive the best care possible.

Moreover, there is generally a shortage of trained sonographers, and the time to properly train a sonographer can be significant. For example, the training can require that a sonographer candidate study, in real time, a variety of patient conditions across a number of patients, which usually results in many visits to care facilities over a long time duration (e.g., months or years). Hence, there can be a lack of trained sonographers, so that patients may not receive the best care possible.

Additionally, trauma bays are often crowded, chaotic spaces within the emergency department where many things are happening at the same time. Each person around the patient's bed has a role and getting access to the patient to perform an ultrasound exam is difficult. Typically, the care of the trauma patient is overseen by the attending physician who is gathering input from many sources around the patient and then directing the care. Often the attending physician cannot see all the information they need, especially from the ultrasound system, in a single location. For example, at times, a critical clinical resource may need to leave their position to allow the ultrasound machine to be moved closer to the bedside for the critical ultrasound exam.

Speed is often of paramount importance when establishing a diagnosis for a trauma patient. The physician must address the most critical issue first and work on secondary issues as they arise. Many of the exams used in the trauma bay, such as extended focused assessment with sonography for trauma (EFAST), rapid ultrasound for shock and hypotension (RUSH), etc., require views of the patient's anatomy from various locations on the patient's body. At times, those locations may be inaccessible from the side of the patient the ultrasound scanner is on. Currently, one physician is assigned to perform ultrasound examinations in the trauma bay and the ultrasound system is often only viewable by that physician. They can scan one region of the body at a time, and the patient data file is limited to one device.

SUMMARY

Systems and methods for a virtual sonography team are described. In some embodiments, an ultrasound system includes an ultrasound scanner that is configured to, as part of an ultrasound examination administered with the ultrasound system, generate ultrasound data based on reflections of ultrasound signals transmitted by the ultrasound scanner and communicate, over a communication network, the ultrasound data to at least one display device and an archiver. An ultrasound machine is coupled to the ultrasound scanner. The ultrasound machine is configured to determine examination data for the ultrasound examination and communicate, over the communication network, the examination data to the archiver. At least one display device is coupled to the communication network. The at least one display device is configured to generate an ultrasound image based on the ultrasound data as part of the ultrasound examination and communicate the ultrasound image to the archiver for aggregation with the examination data into a patient record of the ultrasound examination.

In some embodiments, an ultrasound system includes an ultrasound scanner that is configured to, as part of an ultrasound examination administered with the ultrasound system, generate ultrasound data based on reflections of ultrasound signals transmitted by the ultrasound scanner and communicate, over a communication network, the ultrasound data to a display device and an archiver. The display device is coupled to the communication network. The display device is configured to generate, with a neural network implemented at least partially in hardware of the display device, an inference based on the ultrasound data and communicate the inference, over the communication network, to the archiver for aggregation with the ultrasound data into a patient record of the ultrasound examination.

In some embodiments, a method is implemented by an ultrasound system to perform an ultrasound examination. The method includes communicating one or more tasks of the ultrasound examination to one or more display devices that are wirelessly coupled to an ultrasound scanner via a communication network and transmitting, from the ultrasound scanner and over the communication network, ultrasound imaging data to the one or more display devices. The method also includes generating, with the one or more display devices, ultrasound examination data based on the ultrasound imaging data and the one or more tasks and instructing an archiver to aggregate the ultrasound examination data from the one or more display devices into a patient record of the ultrasound examination.

Other systems, machines and methods for a virtual sonography team are also described.

BRIEF DESCRIPTION OF THE DRAWINGS

The appended drawings illustrate examples and are, therefore, exemplary embodiments and not considered to be limiting in scope.

FIG. 4 is a data flow diagram of a process implemented by an ultrasound system for a virtual sonography team according to some embodiments.

FIG. 5 is a data flow diagram of a process implemented by an ultrasound system for a virtual sonography team according to another embodiment.

FIG. 8 is a data flow diagram of a process implemented by an ultrasound system to perform an ultrasound examination according to some embodiments.

DETAILED DESCRIPTION

Figure 1A:
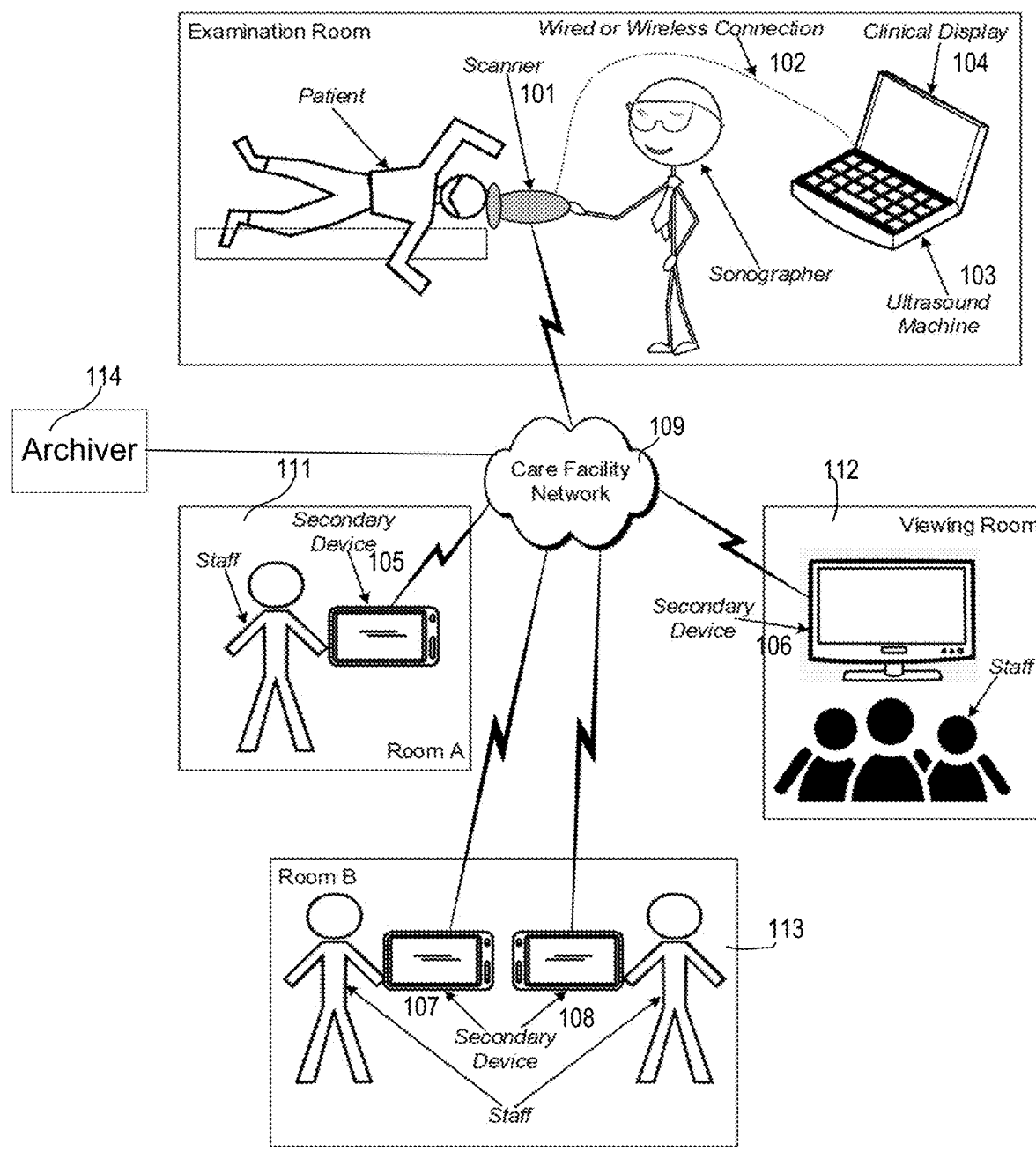
FIG. 1A is a view illustrating an environment of an ultrasound system for a virtual sonography team according to some embodiments.

Systems and methods for a virtual sonography team are described. In some embodiments, an ultrasound system includes an ultrasound scanner that, as part of an ultrasound examination administered with the ultrasound system, generates ultrasound data based on reflections of ultrasound signals transmitted by the ultrasound scanner and communicates the ultrasound data over a communication network to at least one display device and an archiver. An ultrasound machine is coupled to the ultrasound scanner. The ultrasound machine determines examination data for the ultrasound examination and communicates the examination data over the communication network to the archiver. Each display device is coupled to the communication network. Each display device generates an ultrasound image based on the ultrasound data as part of the ultrasound examination and communicates the ultrasound image to the archiver for aggregation with the examination data into a patient record of the ultrasound examination.

Embodiments described herein are directed to ultrasound systems that enable a virtual sonography team, allowing the sharing of sonography duties, in real-time, between the sonographer who is performing an ultrasound examination on a patient, and one or more staff (e.g., doctors, nurses, clinicians, etc.) who are collocated in the same care facility as the sonographer. Moreover, embodiments described herein are directed to ultrasound systems that enable students (e.g., sonographer candidates) to reduce the training time required to become a certified sonographer, compared to training with conventional ultrasound systems.

Reference in the specification to "one example", "an example", "one embodiment" or "an embodiment" means that a particular feature, structure, or characteristic described in conjunction with the embodiment can be included in at least one embodiment. The appearances of the phrases "in one embodiment" or "in an embodiment" in various places in the specification do not necessarily all refer to the same embodiment. The processes depicted in the figures that follow are performed by processing logic that comprises hardware (e.g., circuitry, dedicated logic, etc.), software, firmware, or a combination thereof. Although the processes are described below in terms of some sequential operations, it should be appreciated that some of the operations described may be performed in a different order. Moreover, some operations may be performed in parallel rather than sequentially.

In the specification, the term "and/or" describes that three relationships between objects may exist. For example, A and/or B may represent the following cases: only A exists, both A and B exist, and only B exist, where A and B may be singular or plural.

Ultrasound systems usually take up a lot of space, and have a single display that multiple personnel may wish to observe. However, generally only one person (e.g., a sonographer) can capture images and video clips at a time, obstructing the view of the display screen for other staff, since observing anatomical details closely, even with large screens, is limited to within a few feet of the screen. Further, in the education realm, students (e.g., sonographer candidates) may take quite a long time to come across a wide variety of patient conditions, so each student must complete each activity with a unique patient.

FIG. 1A is a view 100 illustrating an environment of an ultrasound system for a virtual sonography team according to some embodiments. As shown in FIG. 1A, the ultrasound system includes a primary device that includes an ultrasound scanner 101, an ultrasound machine 103, and a clinical display 104 and one or more secondary devices, e.g., secondary devices 105, 106, 107 and 108, collectively, 105-108. In some embodiments, each of the scanner 101, ultrasound machine 103 and clinical display 104 is a portable device. In some embodiments, ultrasound machine 103 is a smart phone, or other portable device that includes a processor and a memory coupled to the processor to perform methods described herein. In some embodiments, clinical display 104 is a display on the smart phone. In some embodiments, scanner 101 includes an ultrasound probe with a transducer array. Scanner 101 can be operated by a sonographer in an examination room (e.g., in an emergency department of the care facility), and can be connected to the ultrasound machine and/or clinical display in the examination room via a wired or wireless connection 102. In some embodiments, the scanner 101 wirelessly communicates with the one or more secondary devices, while the ultrasound machine 103 and clinical display 104 are not in direct communication with the secondary devices 105-108. That is, the scanner 101 wirelessly communicates with the one or more secondary devices 105-108, so that users can look at the same video stream on their corresponding secondary devices. In some embodiments, the scanner 101 communicates with the one or more secondary devices 105-108 and an archiver 114 in a network 109, e.g., using a multicast data transfer with Wi-Fi. In some embodiments, the archiver 114 includes a server that is connected to network 109. In some embodiments, the archiver 114 includes a processor coupled to a memory to receive ultrasound data from the scanner 101 over network 109. In some embodiments, the network 109 is a local area network, an ad-hoc network, or other network. In some embodiments, the scanner 101 transmits data to the one or more secondary devices 105-108 using a multicast IP address. In some embodiments, the communication between the scanner 101 and the one or more secondary devices 105-108 is a bidirectional communication. For example, the scanner operated by a sonographer can transmit ultrasound data to a secondary device at a physician site, and the physician can communicate a feedback regarding the scanned ultrasound data back to the scanner. In some embodiments, the ultrasound system includes an audio channel to provide communication between a sonographer operating the scanner and a user associated with the one or more secondary devices.

The secondary devices can be operated by one or more staff (e.g., doctors, nurses, clinicians, etc.) And students who are collocated in the same care facility as the sonographer who operates the scanner, ultrasound machine, and clinical display. As shown in FIG. 1A, a secondary device 105 is in a room A 111, a secondary device 106 is in a viewing room 112 and secondary devices 107 and 108 are in a room B 113. In some embodiments, the secondary device includes a smart phone, or other portable device that includes a processor and a memory coupled to the processor to perform methods described herein. In some embodiments, a display of the secondary device is a display on the smart phone, or a wearable heads-up device, such as a Google™ Glass. In some embodiments, students capture their own images/clips, perform analysis/measurements and annotate the study, as described in further detail below.

The sonographer and the one or more staff members make up a virtual sonography team. In an example, the one or more staff members are located in a room of the care facility that is separate from the examination room (e.g., a viewing room 112), and secondary device 106 includes a large screen viewing device that can be simultaneously viewed by the one or more staff members. Additionally or alternatively, the one or more staff members can be located in one or more rooms of the care facility that are separate from the examination room (e.g., a hallway, offices, or dedicated viewing rooms), and the secondary device can include one or more viewing devices, one for each of the one or more staff members. Additionally or alternatively, the one or more staff members can be located in an edge or corner of the examination room, away from the ultrasound machine and sonographer. Rooms A and B in FIG. 1A are examples of rooms within a care facility that can be occupied by one or more staff members of the virtual sonography team operating a secondary device.

These staff members may simultaneously and in real-time during the ultrasound examination operate the secondary devices to perform duties usually dedicated to the sonographer, such as saving images, annotating images, performing measurements, running artificial intelligence (AI) routines, archiving, and the like, thus offloading the responsibilities of the sonographer and allowing the sonographer to concentrate on the patient. Further, these staff members can provide instructions/insights to the sonographer. Accordingly, the virtual sonography team can provide superior patient care compared to a sonographer operating a conventional ultrasound system. In one example, a member of the virtual sonography team other than the sonographer records patient biometric data and shares that data with the sonographer and other team members. The secondary devices can use the same archiving mechanism as the ultrasound machine, and/or a distinctly separate set of archivers including archiver 114.

Figure 1B:
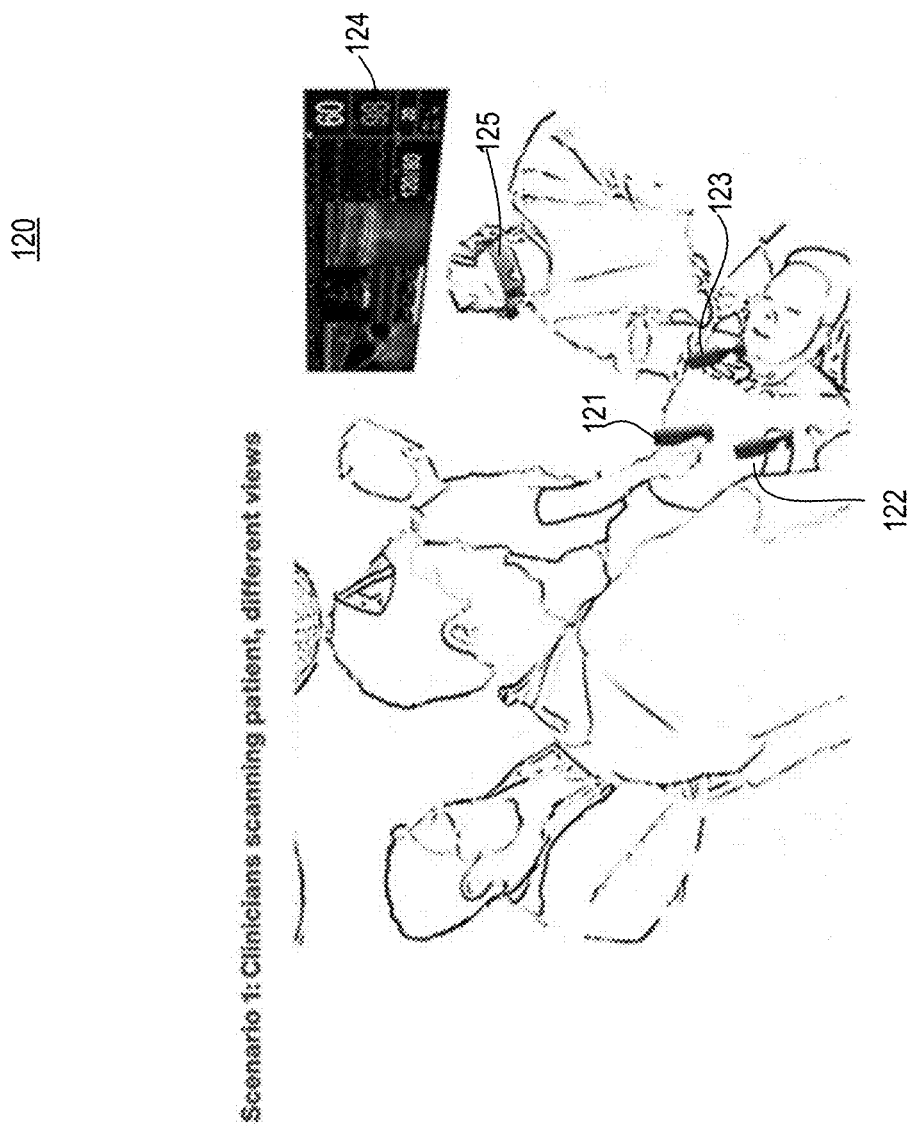
FIG. 1B is a view illustrating an environment of an ultrasound system for a virtual sonography team including multiple scanners according to some embodiments.

FIG. 1B is a view 120 illustrating an environment of an ultrasound system for a virtual sonography team including multiple scanners according to some embodiments. In some embodiments, the ultrasound system illustrated in FIG. 1B represents a portion of the ultrasound system illustrated in FIG. 1A. As shown in FIG. 1B, the ultrasound system includes multiple ultrasound scanners, such as an ultrasound scanner 121, an ultrasound scanner 122 and an ultrasound scanner 123 that can simultaneously generate ultrasound data. In one example, ultrasound scanner 121 is configured to, as part of an ultrasound examination administered with the ultrasound system, generate ultrasound data based on reflections of ultrasound signals transmitted by the ultrasound scanner 121 and communicate the ultrasound data, over a communication network, to at least one of a display device 124 and a display device 125. The one or more additional ultrasound scanners, such as ultrasound scanner 122 and ultrasound scanner 123, are configured to, as part of the ultrasound examination, generate additional ultrasound data based on reflections of additional ultrasound signals transmitted by the one or more additional ultrasound scanners and communicate, over the communication network, the additional ultrasound data to at least one of the display device 124 and display device 125. In some embodiments, display device 124 includes a wall mounted display device. In some embodiments, display device 125 includes a heads-up display configured to be worn by an operator during the ultrasound examination and display an image based on at least one of the ultrasound data and the additional ultrasound data. In some embodiments, the display device of the ultrasound system is configured to, as part of the ultrasound examination, display simultaneously an ultrasound image based on the ultrasound data and an additional ultrasound image based on the additional ultrasound data, as described in further detail below.

In an example, ultrasound scanners 121, 122, and 123 operate simultaneously according to a system clock provided to the ultrasound scanners 121, 122, and 123. The system clock can control the transmission of ultrasound from each of the scanners, so that the effective radiated power to the patient can be reduced compared to all of the scanners 121, 122, and 123 transmitting ultrasound at the same time. The system clock can allow for the gating of transmitted ultrasound from the scanners, so that at some time intervals, less than all (e.g., only one) of the scanners is actively transmitting ultrasound. At other times, the system clock can provide for overlapping ultrasound transmissions, so that two or more of the scanners 121, 122, and 123 can transmit ultrasound at the same time. The system clock can be generated by one of the ultrasound scanners, the ultrasound machine 103, a server, or any suitable device. In an embodiment, the system clock is generated based on the anatomy being imaged or a type of ultrasound examination. For instance, for a cardiac examination, the system clock can be generated so that the scanners 121 and 122 transmit ultrasound at the same time, and the scanner 123 transmits ultrasound while the scanners 121 and 122 are not transmitting ultrasound. For a lung examination, the system clock can be generated so that the scanners 121, 122, and 123 overlap their transmissions of ultrasound for no more than 20% of a specified time period, e.g., one second.

Figure 1C:
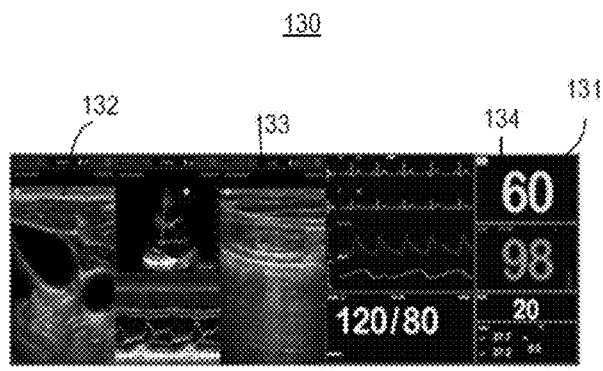
FIG. 1C is a view illustrating a display device of the ultrasound system according to some embodiments.

FIG. 1C is a view 130 illustrating a display device 131 of the ultrasound system according to some embodiments. In some embodiments, display device 131 represents display device 124. As shown in FIG. 1C, display device 131 is configured to, as part of the ultrasound examination, display simultaneously an ultrasound image 132 based on the ultrasound data (e.g., from a first ultrasound scanner) and an additional ultrasound image 133 based on the additional ultrasound data (e.g., from a second ultrasound scanner). In some embodiments, display device 131 is a wall mounted display that aggregates one or more ultrasound images (scans) and patient information 134 to give the attending physician a complete view of the patient's status at a time.

Figure 1D:
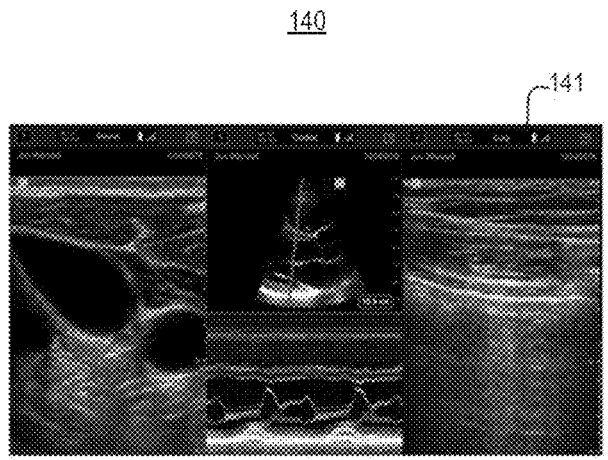
FIG. 1D is a view illustrating a display device of the ultrasound system according to some embodiments.

FIG. 1D is a view 140 illustrating a display device 141 of the ultrasound system according to some embodiments. In some embodiments, display device 141 represents display device 124. In some embodiments, multiple saved images, clips, measurements and calculations are aggregated into the common patient record and can be presented on display device 141.

In some embodiments, the ultrasound scanner is implemented to transmit the ultrasound signals at a patient anatomy and the additional ultrasound scanner is implemented to transmit the additional ultrasound signals at the patient anatomy. Referring back to FIG. 1B, ultrasound scanners 121, 122 and 123 can scan the same anatomy of the patient from different views. The ultrasound system can include a processor implemented to generate a three-dimensional (3D) image of the patient anatomy based on the ultrasound data and the additional ultrasound data. The display device can be implemented to display the 3D image simultaneously with the ultrasound image and the additional ultrasound image.

Figure 1E:
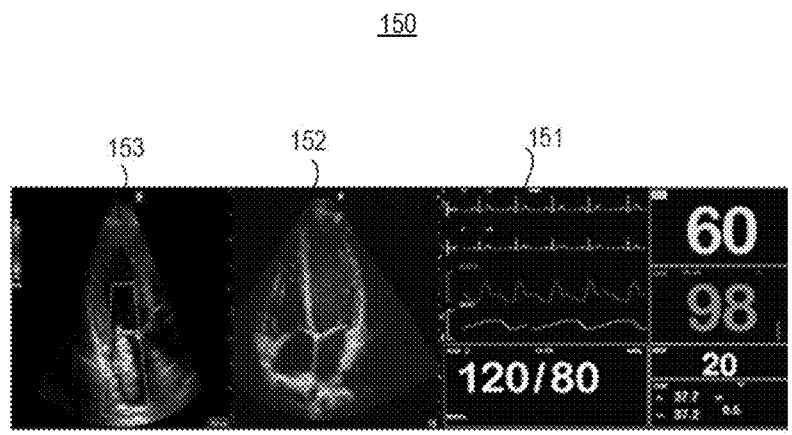
FIG. 1E is a view illustrating a display device of the ultrasound system according to some embodiments.

FIG. 1E is a view 150 illustrating a display device 151 of the ultrasound system according to some embodiments. In some embodiments, display device 151 represents display device 124. As shown in FIG. 1E, the display device 151 displays a 3D ultrasound image 152 and an ultrasound image 153. In some embodiments, 3D ultrasound image 152 is generated based on the ultrasound scans of the same anatomy of the patient from different views by multiple scanners (e.g., at least two of the scanners 121, 122 and 123). In some embodiments, ultrasound image 153 is generated based on the ultrasound scan of the patient anatomy by one of the scanners 121, 122, 123.

Figure 1F:
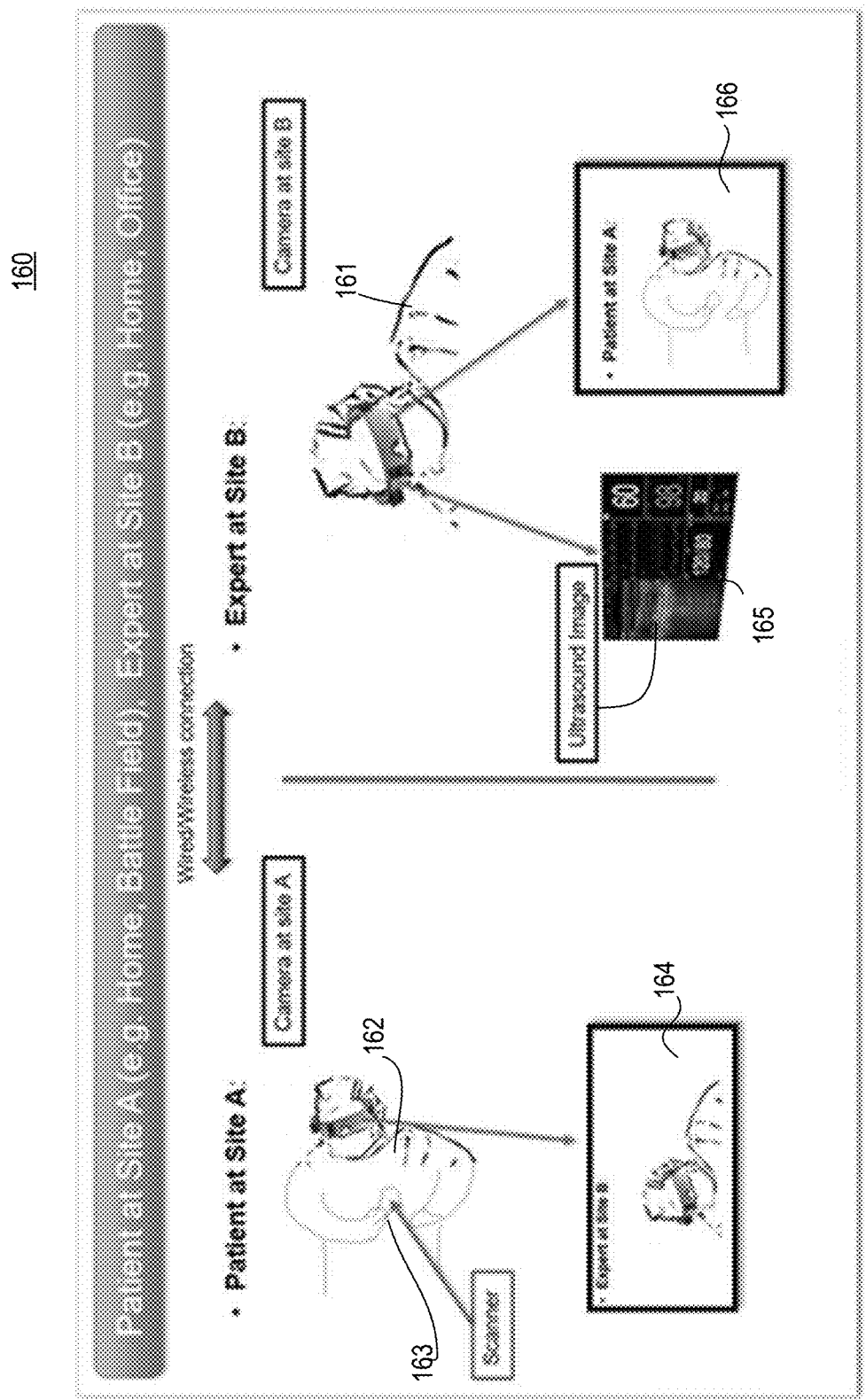
FIG. 1F is a view illustrating an environment of an ultrasound system for a virtual sonography team at two different locations according to some embodiments.

FIG. 1F is a view 160 illustrating an environment of an ultrasound system for a virtual sonography team at two different locations according to some embodiments. The environment of the ultrasound system for a virtual sonography team includes a location A and a location B that communicate via a wired and/or wireless connection. Each of the locations A and B has a camera/microphone and at least one display device. As shown in FIG. 1F, an ultrasound scanner 163 is operated by a patient 162 at location A and a display device 165 and a display device 166 are operated by a sonographer (expert) at a location B that is different from the location A. As shown in FIG. 1F, expert 161 at site B guides patient 162 (who may be wounded in the battle-field or contagious with a virus) at site A with placement of the ultrasound scanner 163 to make a diagnosis. The patient 162 sees the expert on a display device 164 at site B and operates the scanner 163. The expert 161 sees the patient on display device 166 and an ultrasound image with additional medical information on display device 165 at site B.

Figure 2:
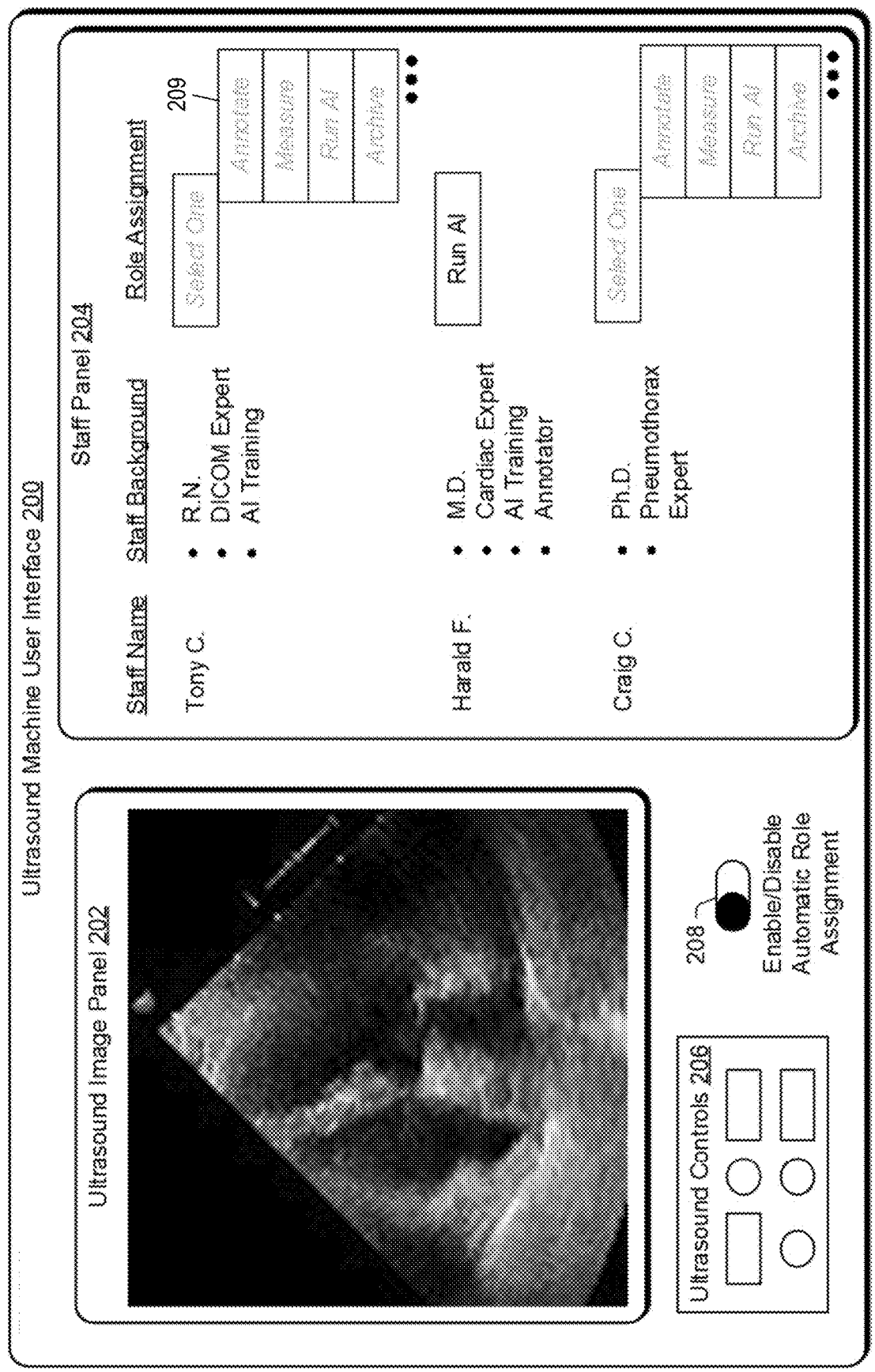
FIG. 2 is a view of a user interface of the ultrasound machine used by a sonographer to assign roles and/or tasks to one or more staff members of a virtual sonography team according to some embodiments.

FIG. 2 illustrates a view of a user interface 200 of an ultrasound machine used by a sonographer to assign roles and/or tasks to one or more staff members of a virtual sonography team according to some embodiments. The user interface 200 can be displayed by ultrasound machine 103 in FIG. 1A, such as on clinical display 104 or on the display of a device coupled to the ultrasound machine 103, e.g., a tablet or smart phone (not shown). Referring to FIG. 2, user interface 200 includes an ultrasound image panel 202 that displays an ultrasound image and can also display any suitable ultrasound data, such as scanner settings, scanner temperature, imaging parameters, etc. In some embodiments, user interface 200 includes a staff panel 204 that displays background information for staff members of the virtual sonography team having devices connected to a scanner displayed in user interface 200, such as a staff member name, background information of the staff member (e.g., user identification data) and roles assigned to the staff, manually by the sonographer or automatically by the ultrasound system. In the example in FIG. 2, roles and/or tasks for staff members Tony C. and Craig C. have not yet been assigned, and can be selected by the sonographer from the drop down menus in the staff panel 204, such as a drop down menu 209. The drop down menus can indicate any suitable roles and/or tasks to reduce the burden on the sonographer, including to annotate ultrasound images, perform measurements on the ultrasound images, run AI algorithms, archive images, etc. As shown in FIG. 2, the role for staff member Harald F. has been assigned as "Run AI", indicating that this staff member is responsible for running AI algorithms during the ultrasound examination. In some embodiments, functionalities associated with the roles/tasks are limited by preset rules to prevent certain users from performing predetermined functions or gaining access to certain data. Such preset rules can allow certain users to perform or have access to certain predetermined functions and/or data. In some embodiments, the functionalities are limited by a role assigned to a user. For example, Tony C. who is a registered nurse and a DICOM expert can be assigned a role/task to archive the ultrasound images and be prevented from doing a cardiac expertise task.

In some embodiments, the sonographer controls which secondary devices are allowed to connect to the scanner. The sonographer assigns roles and/or tasks to the one or more staff members, and the roles and/or tasks are communicated from the scanner to the secondary devices. For example, the sonographer can designate a first staff member (personnel) to annotate images, a second staff personnel to record/save images, a third staff personnel to run a first type of AI routine, and a fourth staff personnel to run a second type of AI routine. The sonographer can enter these selections into staff panel 204 of the ultrasound machine, which can communicate the sonographer's selections to the scanner. In turn, the sonographer can assign the roles and/or tasks to the staff personnel using the scanner by wirelessly transmitting data indicating the selections made by the sonographer to the respective secondary devices operated by the staff personnel.

In some embodiments, the ultrasound system automatically (e.g., without explicit assignments selected by the sonographer) assign roles and/or tasks to the one or more staff members. For example, the ultrasound system can determine the one or more staff members of the virtual sonography team from user identification data communicated from the secondary devices to the scanner, and based on the user identification data, assign the roles and/or tasks. The user identification data can include any suitable data of the one or more staff, such as a job title, an expertise, a training history, and other data. The ultrasound system can then assign the roles and/or tasks to best suit the background of the staff, such as by assigning the role of running AI routines to one or more staff members who have undergone training on AI algorithms, as indicated by the user identification data. In some embodiments, the sonographer needs to enable the automatic role assignment via the ultrasound machine, such as by selecting a menu option displayed on a user interface of the clinical display to allow automatic role assignment, with the default option indicating no automatic role assignment is enabled (see switch 208, described below).

As shown in FIG. 2, user interface 200 includes user controls 206 for controlling the ultrasound machine, such as controls for gain, depth, presets, drive signals, filters, pulse widths, and other controls. User interface 200 also includes a switch 208, which can be set to enable or disable automatic role assignment to the staff members by the ultrasound system, based on the staff background information indicated in staff panel 204. In the example shown in FIG. 2, automatic role assignment is disabled, and the sonographer may assign roles via staff panel 204. When switch 208 is disabled, a sonographer can assign roles to virtual sonography team members for ultrasound examination. When switch 208 is enabled the ultrasound system automatically assigns roles/tasks based on the background information of the virtual sonography team members.

In some embodiments, because the virtual sonography team contains members who are collocated (e.g., within the same building or complex of buildings making up a care facility), communication between the scanner and the secondary devices does not require the Internet. In some embodiments, data is communicated between the scanner and the secondary devices using a network dedicated to the care facility, such as a local area network (LAN). Hence, not only is the data kept secure compared to data that is part of Internet communications, it is also technically possible to communicate ultrasound data between the scanner and secondary devices. For instance, data associated with ultrasound examinations is often constructed according to a protocol so that the ultrasound data is not routable over the Internet, preventing remote, real-time distribution of sonography roles over the Internet during an ultrasound examination.

In some embodiments, multicast data may not be routable across subnets of a network. In these cases, the ultrasound system generates a separate "starter" multicast address to initiate the communications between the scanner and multiple secondary devices. The ultrasound system also generates a final multicast address and encryption information and provides the final multicast address and encryption information to the secondary devices.

In some embodiments, the ultrasound system enables students (e.g., sonographer candidates) to connect to scanners within a care facility that significantly reduces the training time required to become a certified sonographer, compared to training with conventional ultrasound systems. For example, the ultrasound system can allow students located within a care facility, such as in a training room, to connect a secondary device to one of multiple scanners that are active in the care facility, with different patients. Hence, the student can have access to multiple patients with multiple conditions in a single visit to a care facility, from a single location within the care facility. In some embodiments, the secondary device operated by a student has a user interface that displays a list of active and/or scheduled ultrasound examinations within the care facility. The student may be able to select one of the ultrasound examinations and connect their secondary device to a scanner for a desired type of examination. In this way, the student can quickly determine a suitable examination based on the student's needs, such as to fulfill a list of required types of examinations, and thereby reduce the time needed to complete the sonographer training.

Figure 3:
FIG. 3 is a view of user interfaces of a display device of an ultrasound system used by a virtual sonography team member according to some embodiments.

FIG. 3 illustrates a view 300 of user interfaces of a display device of an ultrasound system used by a virtual sonography team member according to some embodiments, e.g., one or more of the secondary devices 105-108. A user interface 301 includes an ultrasound imaging screen that displays an ultrasound image and a set of controls 303. Controls 303 are selectable to capture an ultrasound image, capture an ultrasound clip, connect/pair with other devices (e.g., a scanner), provide patient information, review, control imaging settings, control ultrasound machine/scanner settings, display an amount of time (e.g., minutes) remaining for scanning, and the like. In some embodiments, a primary device (e.g., ultrasound machine 103 in FIG. 1) sets depth/2D/3D/color and authorizes secondary users. In another embodiment, a designated secondary device (e.g., at a physician's site) sets depth/2D/3D/color and authorizes a sonographer and other secondary users. In some embodiments, secondary devices, such as secondary devices 105-108 receive every image frame that the primary device receives, capture images and clips, set clip duration, prospective/retro imaging, etc. In some embodiments, the primary and secondary devices add notes and annotations. In some embodiments, any of the display devices of the ultrasound system updates patient biometrics prior to saving a first ultrasound image.

As shown in FIG. 3, a user interface 302 is displayed on the display device connected to an ultrasound scanner according to some embodiments. In some embodiments, user interface 302 is displayed prior to displaying user interface 301. As shown in FIG. 3, user interface 302 displays a message to a user to scan a barcode on the scanner to connect the display device with the scanner. In some embodiments, the barcode on the scanner housing allows a registered ultrasound application to connect to a network. If the barcode is damaged, a connection digit sequence can be entered manually in a manual entry of connection information field 304. In some embodiments, imaging settings control is active when the display device is connected to the scanner, allowing the operator of the display device to control imaging parameters for images displayed on the display device. User interface 302 includes a set of controls 305 to set imaging settings, and return to user interface 301 that includes the ultrasound imaging screen.

In some embodiments, multiple individuals (e.g., students, etc.) can connect to a scanner to receive live ultrasound images. In the case of these individuals being students, the students can practice capturing video clips and images, annotating studies, all from a single sonographer using the scanner on a single patient. In this way, the training of students is made more efficient than training with conventional ultrasound systems, in which it is difficult or impossible to simultaneously train multiple students during a single ultrasound examination.

In some embodiments, a care facility can participate in a consortium of care facilities for the purpose of training students. A student can view, via a user interface of their secondary device, scheduled ultrasound examinations within a care facility of the consortium, "typical" types of examinations associated with a care facility or a department within the care facility (e.g., one department can be associated with respiratory issues, another department can be associated with determining a type of cancer, and still another department can be associated with managing pain), etc. The student can then determine which department of which care facility to visit, and the schedule of the visit, to connect their secondary device to an appropriate scanner and advance their sonography training. This training can significantly reduce the time needed for the student to be exposed to ultrasound examinations of multiple patients with multiple conditions, compared to conventional training methods that do not a priori expose information about scheduled or typical types of ultrasound examinations for training. Moreover, the training methods disclosed herein facilitate training with live, real-time ultrasound examinations, rather than studies of previously-recorded examinations. Hence, the student is exposed to the real-world pace of ultrasound examinations, which can be difficult to understand from study of pre-recorded data.

FIG. 4 is a data flow diagram of a process 400 implemented by an ultrasound system for a virtual sonography team according to some embodiments. The process is performed by processing logic that may comprise hardware (circuitry, dedicated logic, etc.), software (such as is run on a general-purpose computer system or a dedicated machine), firmware, or combinations thereof. In some embodiments, the ultrasound system includes an ultrasound scanner, an ultrasound machine coupled to the ultrasound scanner and at least one display device coupled to the ultrasound machine, as described above. In some embodiments, the ultrasound system includes one or more processors and a memory coupled to the processor(s) to perform the process, and the one or more processors are coupled to the ultrasound scanner, the ultrasound machine and the display device to perform process 400.

Referring to FIG. 4, process 400 includes processing logic generating ultrasound data based on reflections of ultrasound signals transmitted by the ultrasound scanner and communicating the ultrasound data, over a communication network, to at least one display device and an archiver at block 401. In some embodiments, processing logic generates and communicates the ultrasound data using one or more processors of an ultrasound scanner. In some embodiments, the ultrasound scanner communicates to the at least one display device, via the communication network, a task to be performed during the ultrasound examination with the at least one display device. In some embodiments, the ultrasound scanner can receive, via the communication network and from the at least one display device, operator data for the at least one display device, and the ultrasound scanner and/or the ultrasound machine determine the task based on the operator data automatically and without user intervention. In some embodiments, each ultrasound scanner and/or the ultrasound machine receives a user selection that indicates the task.

Process 400 continues at block 402 where processing logic determines examination data for the ultrasound examination and communicates the examination data to the archiver over the communication network. The determination can be performed by the one or more processors of an ultrasound machine. In some embodiments, the examination data includes at least one of biometric patient data, patient identification data, an additional ultrasound image, and an imaging parameter.

At block 403, processing logic generates an ultrasound image based on the ultrasound data as part of the ultrasound examination and communicates the ultrasound image to the archiver for aggregation with the examination data into a patient record of the ultrasound examination. The generation of the ultrasound image can be performed by one or more processors and displayed using the display device. In some embodiments, the ultrasound data includes pre-scan-converted image data and the at least one display device is implemented to convert the pre-scan-converted image data into scan-converted image data to generate the ultrasound image.

In some embodiments, the ultrasound scanner and the ultrasound machine are located in a first room of a care facility and the at least one display device is located in a second room of the care facility. In some embodiments, the ultrasound scanner, the ultrasound machine, and at least one display device are located in a same room of a care facility, and the ultrasound scanner and the ultrasound machine are operated by a first user and the at least one display device is operated by a second user during the ultrasound examination. In some embodiments, the display device includes a neural network that generates, based on the ultrasound data, at least one of a label, a classification, a segmentation, and a probability and the display device communicates to the archiver the at least one of the label, the classification, the segmentation, and the probability for aggregation into the patient record.

FIG. 5 is a data flow diagram of a process 500 implemented by an ultrasound system for a virtual sonography team according to another embodiment. The process is performed by processing logic that may comprise hardware (circuitry, dedicated logic, etc.), software (such as is run on a general-purpose computer system or a dedicated machine), firmware, or combinations thereof. In some embodiments, the ultrasound system includes an ultrasound scanner, an ultrasound machine coupled to the ultrasound scanner and at least one display device coupled to the ultrasound machine, as described above. In some embodiments, the display device includes a server device. In some embodiments, the ultrasound system includes one or more processors and a memory coupled to the processor(s) to perform the process, and the one or more processors are coupled to the ultrasound scanner, the ultrasound machine and the display device to perform process 500.

Referring to FIG. 5, process 500 starts at block 501 with processing logic generating by the one or more processors of an ultrasound scanner, ultrasound data based on reflections of ultrasound signals transmitted by the ultrasound scanner and communicating, over a communication network, the ultrasound data to a display device and an archiver, as described above. In some embodiments, the display device generates an ultrasound image based on the ultrasound data and displays the ultrasound image, as described above. At block 502, processing logic generates an inference by the one or more processors with a neural network implemented at least partially in hardware of the display device, based on the ultrasound data. Processing logic communicates the inference over the communication network and to the archiver for aggregation with the ultrasound data into a patient record of the ultrasound examination, as described above. In some embodiments, the inference includes at least one of a label, a classification, a segmentation, and a probability. For example, the inference can include a classification of a vein versus an artery, a heart versus a kidney, or other classification. In some embodiments, the ultrasound system includes an archiver, as described above, and process 500 continues at block 503 where processing logic communicates the patient record, over the communication network, to a database of a care facility where the ultrasound examination is performed, as described above. In some embodiments, processing logic performs this communication using one or more processors of an archiver.

Figure 6:
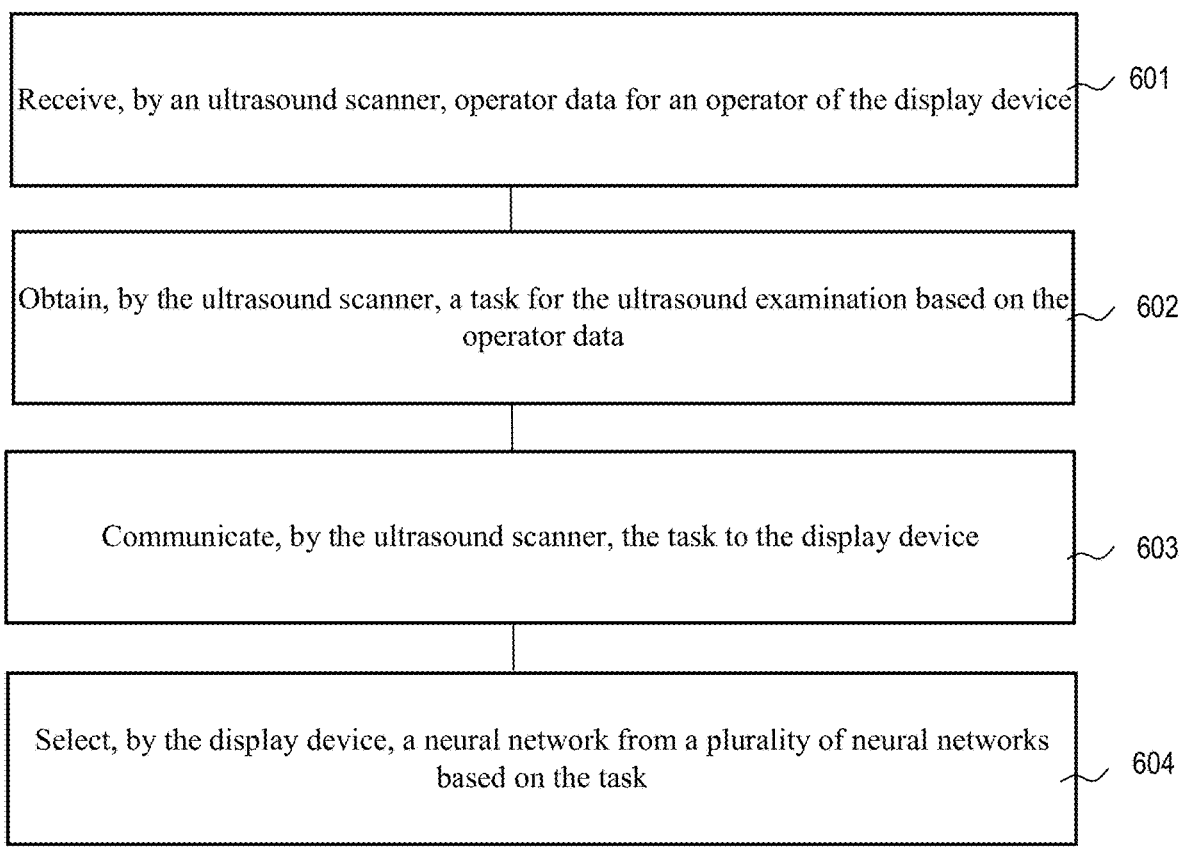
FIG. 6 is a data flow diagram of a process implemented by an ultrasound system for a virtual sonography team according to another embodiment.

FIG. 6 is a data flow diagram of a process 600 implemented by an ultrasound system for a virtual sonography team according to another embodiment. The process is performed by processing logic that may comprise hardware (circuitry, dedicated logic, etc.), software (such as is run on a general-purpose computer system or a dedicated machine), firmware, or combinations thereof. In some embodiments, the ultrasound system includes an ultrasound scanner, an ultrasound machine coupled to the ultrasound scanner and at least one display device coupled to the ultrasound machine, as described above. In some embodiments, the ultrasound system includes one or more processors and a memory coupled to the processor(s) to perform the process, and the one or more processors are coupled to the ultrasound scanner, the ultrasound machine and the display device to perform process 600.

Referring to FIG. 6, process 600 starts at block 601 with processing logic receiving operator data for an operator of the display device, as described above. In some embodiments, processing logic receives the operator data using one or more processors of an ultrasound scanner. At block 602, processing logic obtains a task for the ultrasound examination based on the operator data, and at block 603, the processing logic communicates the task to the display device. In some embodiments, processing logic obtains and communicates the task using one or more processors of an ultrasound scanner.

At block 604, processing logic selects a neural network from a plurality of neural networks based on the task. In some embodiments, the neural network is implemented at least partially in hardware of the display device, as described above. In some embodiments, processing logic performs the selection using one or more processors of the display device.

Figure 7:
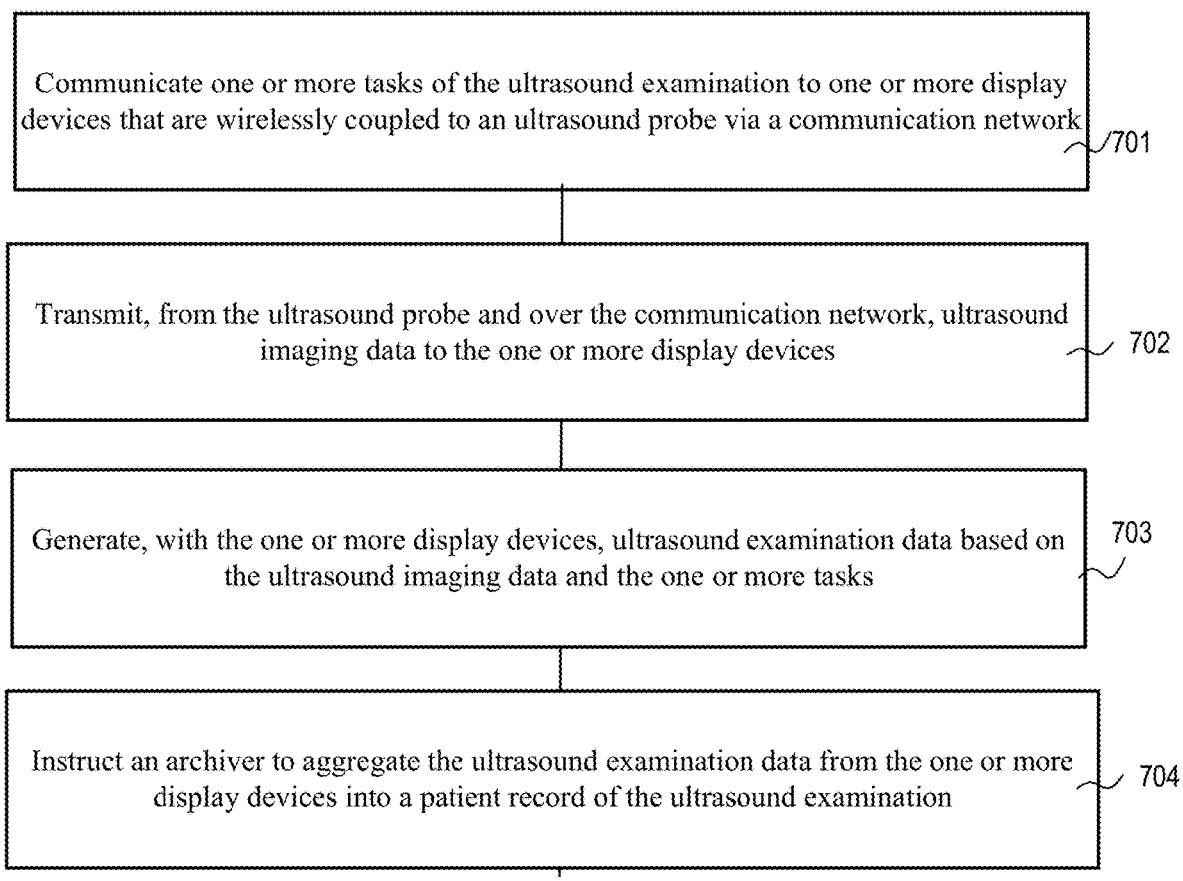
FIG. 7 is a data flow diagram of a process implemented by an ultrasound system to perform an ultrasound examination according to some embodiments.

FIG. 7 is a data flow diagram of a process 700 implemented by an ultrasound system to perform an ultrasound examination according to some embodiments. The process is performed by processing logic that may comprise hardware (circuitry, dedicated logic, etc.), software (such as is run on a general-purpose computer system or a dedicated machine), firmware, or combinations thereof. In some embodiments, the ultrasound system includes an ultrasound scanner, an ultrasound machine coupled to the ultrasound scanner and at least one display device coupled to the ultrasound machine, as described above. In some embodiments, the ultrasound system includes one or more processors and a memory coupled to the processor(s) to perform the process, and the one or more processors are coupled to the ultrasound scanner, the ultrasound machine and the display device to perform process 700.

Referring to FIG. 7, process 700 starts at block 701 with processing logic communicating one or more tasks of the ultrasound examination to one or more display devices that are wirelessly coupled to an ultrasound scanner via a communication network. At block 702, processing logic transmits ultrasound imaging data from the ultrasound scanner and over the communication network to the one or more display devices.

At block 703, processing logic generates ultrasound examination data based on the ultrasound imaging data and the one or more tasks. In some embodiments, processing logic generates the ultrasound examination data by the one or more processors with the one or more display devices. In some embodiments, the ultrasound system includes an archiver coupled to the one or more display devices. At block 704, processing logic instructs an archiver to aggregate the ultrasound examination data from the one or more display devices into a patient record of the ultrasound examination, as described above.

Typically, in a trauma situation, several clinicians, doctors and/or nurses, could perform a component of a protocol such as EFAST or RUSH. Embodiments described herein enable live data sharing across multiple ultrasound systems and aggregation of the data across all connected ultrasound scanners. In some embodiments of an ultrasound system for a virtual sonography team as described herein all of the connected scan data (e.g., from multiple ultrasound scanners) are available for viewing by the attending physician on a single display, such as, for example, a wall mounted monitor or a handheld tablet. In some embodiments, all patient data, images, clips, measurements, calculations, and reports are captured into a single record.

In some embodiments, data from two separate simultaneous ultrasound scanners are used to perform volume measurements such as, for example, Simpsons for an ejection fraction, providing faster and better answers to the clinicians comparing to conventional techniques.

In some embodiment, data from two or more separate simultaneous ultrasound scanners are used to provide the raw data needed to create 3D and/or 4D ultrasound images.

In some embodiments, the ultrasound system includes an additional ultrasound scanner to generate, as part of the ultrasound examination, additional ultrasound data based on additional reflections of additional ultrasound signals transmitted by the additional ultrasound scanner and communicate, over the communication network, the additional ultrasound data to the at least one display device. For example, ultrasound scanners are placed at different positions to scan the patient to provide different ultrasound imaging views. In some embodiments, the ultrasound system uses different ultrasound imaging views to automatically build an ultrasound image in 3D. In some embodiments, the display device generates an additional ultrasound image based on the additional ultrasound data and a neural network generates, based on the ultrasound image and the additional ultrasound image, at least one of a label, a classification, a segmentation, a probability, and a new ultrasound image. For example, a wall mounted display device can aggregate one or more scans and patient information to give a physician a complete view of the patient's status at one time. In an example, a wearable heads-up device, such as a Google™ Glass can display individual scan information. In some embodiments, the display device communicates, over a communication network and to the archiver, the at least one of the label, the classification, the segmentation, the probability, and the new ultrasound image for the aggregation into the patient record. In some embodiments, the new ultrasound image includes at least one of a super-resolution image and a 3D (three-dimensional) image. For example, all saved ultrasound images, clips, measurements and calculations for the same patient are aggregated into a common patient record that can be provided to multiple devices.

FIG. 8 is a data flow diagram of a process 800 implemented by an ultrasound system to perform an ultrasound examination according to some embodiments. The process is performed by processing logic that may comprise hardware (circuitry, dedicated logic, etc.), software (such as is run on a general-purpose computer system or a dedicated machine), firmware, or combinations thereof. In some embodiments, the ultrasound system includes an ultrasound scanner, an additional ultrasound scanner, an ultrasound machine coupled to the ultrasound scanner and/or the additional ultrasound scanner, and at least one display device coupled to the ultrasound machine, as described above. In some embodiments, the ultrasound system includes one or more processors and a memory coupled to the processor(s) to perform the process, and the one or more processors are coupled to the ultrasound scanner, the ultrasound machine and the display device to perform process 800.

Referring to FIG. 8, process 800 includes processing logic generating ultrasound data based on reflections of ultrasound signals transmitted by the ultrasound scanner and communicating the ultrasound data, over a communication network, to at least one display device and an archiver at block 801. In some embodiments, processing logic generates and communicates the ultrasound data using one or more processors of an ultrasound scanner.

Process 800 continues at block 802 where processing logic determines examination data for the ultrasound examination and communicates the examination data to the archiver over the communication network. The determination can be performed by the one or more processors of an ultrasound machine. In some embodiments, the examination data includes at least one of biometric patient data, patient identification data, an additional ultrasound image, and an imaging parameter.

At block 803, processing logic generates an ultrasound image based on the ultrasound data as part of the ultrasound examination and communicates the ultrasound image to the archiver for aggregation with the examination data into a patient record of the ultrasound examination, as described above with respect to FIG. 4. At block 804, processing logic of an additional ultrasound scanner generates additional ultrasound data based on additional reflections of additional ultrasound signals transmitted by the additional ultrasound scanner and communicates the additional ultrasound data, over the communication network, to at least one display device and the archiver. In some embodiments, processing logic generates and communicates the additional ultrasound data using one or more processors of an additional ultrasound scanner.

At block 805, processing logic generates an additional ultrasound image based on the additional ultrasound data. The generation of the additional ultrasound image can be performed by one or more processors and displayed using the display device. In some embodiments, the ultrasound data includes pre-scan-converted image data and the at least one display device is implemented to convert the pre-scan-converted image data into scan-converted image data to generate the ultrasound image, as described above with respect to FIG. 4.

At block 806, processing logic generates, based on the ultrasound image and the additional ultrasound image, at least one of a label, a classification, a segmentation, a probability, and a new ultrasound image. In some embodiments, processing logic generates the label, classification, segmentation, probability, and/or a new ultrasound image using a neural network. In some embodiments, the new ultrasound image includes at least one of a super-resolution image and a three-dimensional image. In some embodiments, processing logic implements the neural network using one or more processors of an ultrasound scanner and/or an additional ultrasound scanner. At block 807, processing logic communicates, over the communication network and to the archiver, the at least one of the label, the classification, the segmentation, the probability, and the new ultrasound image for aggregation into the patient record. In some embodiments, processing logic communicates the at least one of the label, the classification, the segmentation, the probability, and the new ultrasound image using one or more processors of an additional ultrasound scanner.

As discussed above, in some embodiments the ultrasound system can include multiple ultrasound scanners that can simultaneously generate ultrasound data.

In one example, an ultrasound system includes an ultrasound scanner configured to, as part of an ultrasound examination administered with the ultrasound system, generate ultrasound data based on reflections of ultrasound signals transmitted by the ultrasound scanner and communicate, over a communication network, the ultrasound data to a display device. The ultrasound system can include an additional ultrasound scanner configured to, as part of the ultrasound examination, generate additional ultrasound data based on reflections of additional ultrasound signals transmitted by the additional ultrasound scanner and communicate, over the communication network, the additional ultrasound data to the display device. The ultrasound system can also include the display device configured to, as part of the ultrasound examination, display simultaneously an ultrasound image based on the ultrasound data and an additional ultrasound image based on the additional ultrasound data.

In an embodiment, the ultrasound scanner is implemented to transmit the ultrasound signals at a patient anatomy and the additional ultrasound scanner is implemented to transmit the additional ultrasound signals at the patient anatomy. The ultrasound system can include a processor implemented to generate a three-dimensional (3D) image of the patient anatomy based on the ultrasound data and the additional ultrasound data. The display device can be implemented to display the 3D image simultaneously with the ultrasound image and the additional ultrasound image. Additionally or alternatively, the ultrasound system includes a processor implemented to generate a biometric parameter for the patient anatomy based on the ultrasound data and the additional ultrasound data, and the display device is implemented to display an indicator of the biometric parameter. In an example, the patient anatomy includes a cardiac ventricle and the biometric parameter includes an ejection fraction.

In one embodiment, the ultrasound scanner is implemented to transmit the ultrasound signals at a patient anatomy and the additional ultrasound scanner is implemented to transmit the additional ultrasound signals at a different patient anatomy than the patient anatomy.

In an embodiment, the display device is implemented to communicate, over the communication network, the ultrasound image and the additional ultrasound image to an archiver for aggregation into a patient record of the ultrasound examination. In an example, the display device is configured to implement a neural network to generate, based on the ultrasound image and the additional ultrasound image, at least one of a label, a classification, a segmentation, a probability, and a new ultrasound image. The display device can communicate, over the communication network and to the archiver, the at least one of the label, the classification, the segmentation, the probability, and the new ultrasound image for said aggregation into the patient record.

In one example, the display device, the ultrasound scanner, and the additional ultrasound scanner are located in a common room to perform the ultrasound examination. The display device can be wall mounted in the common room.

In an embodiment, the ultrasound system includes a heads-up display configured to be operator worn during the ultrasound examination and display an image based on at least one of the ultrasound data and the additional ultrasound data. Additionally or alternatively, the ultrasound system can include one more ultrasound scanner configured to, as part of the ultrasound examination, generate at least more ultrasound data and communicate it to a heads-up display. The heads-up display can be configured to be worn during the ultrasound examination by an operator of the one more ultrasound scanner and implemented to display at least one ultrasound image based on the at least more ultrasound data.

In an embodiment, the ultrasound scanner and the additional ultrasound scanner of the ultrasound system are implemented to generate the ultrasound signals and the additional ultrasound signals, respectively, at different center frequencies. Additionally or alternatively, the ultrasound scanner and the additional ultrasound scanner can be implemented to generate the ultrasound signals and the additional ultrasound signals, respectively, at different power levels. In an example, the ultrasound scanner and the additional ultrasound scanner are operated during the ultrasound examination by a same operator. In another example, the ultrasound scanner and the additional ultrasound scanner are operated during the ultrasound examination by different operators.

In one embodiment of the present invention an ultrasound system includes an ultrasound scanner configured to, as part of an ultrasound examination administered with the ultrasound system, generate ultrasound data based on reflections of ultrasound signals transmitted by the ultrasound scanner and communicate wirelessly, over a communication network, the ultrasound data to a display device. The ultrasound system includes an additional ultrasound scanner configured to, as part of the ultrasound examination, generate additional ultrasound data based on reflections of additional ultrasound signals transmitted by the additional ultrasound scanner and communicate wirelessly, over the communication network, the additional ultrasound data to the display device. The ultrasound system also includes the display device configured to, as part of the ultrasound examination, generate, based on the ultrasound data and the additional ultrasound data, an ultrasound image, and display the ultrasound image.

In an example, the display device is configured to, as part of the ultrasound examination, generate an additional ultrasound image based on one of the ultrasound data and the additional ultrasound data, and display, simultaneously with the display of the ultrasound image, the additional ultrasound image. The display device can include a neural network implemented to generate the additional ultrasound image as a 3D image. The display device can be implemented to rotate or translate a point of view of the 3D image. In an example, the display device is implemented to communicate, over the communication network, the ultrasound image and the additional ultrasound image to an archiver for aggregation into a patient record of the ultrasound examination.

In an embodiment, the ultrasound system includes one more ultrasound scanner configured to, as part of the ultrasound examination, generate at least more ultrasound data and communicate it to a heads-up display. The ultrasound system includes the heads-up display configured to be worn during the ultrasound examination by an operator of the one more ultrasound scanner and implemented to display at least one ultrasound image based on the at least more ultrasound data.

In one example, the ultrasound scanner and the additional ultrasound scanner are implemented to generate the ultrasound signals and the additional ultrasound signals, respectively, at different center frequencies or different power levels. In an example, the ultrasound scanner and the additional ultrasound scanner are operated during the ultrasound examination by a same operator. Alternatively, the ultrasound scanner and the additional ultrasound scanner can be operated during the ultrasound examination by different operators. In an example, the ultrasound scanner transmits the ultrasound signals towards a patient anatomy, the additional ultrasound scanner transmits the additional ultrasound signals towards the patient anatomy, and the ultrasound image depicts the patient anatomy.

In an embodiment, the ultrasound system includes a processor implemented to determine a biometric parameter based on the ultrasound data and the additional ultrasound data, and the display device is implemented to display an indicator of the biometric parameter. The biometric parameter can include at least one of a cardiac ejection fraction, a fluid flow rate, an anatomy volume, and a blood vessel diameter.

In one embodiment of the present invention an ultrasound system includes an ultrasound scanner configured to, as part of an ultrasound examination administered with the ultrasound system, generate ultrasound data based on reflections of ultrasound signals transmitted by the ultrasound scanner and communicate wirelessly, over a communication network, the ultrasound data to an aggregator. The ultrasound system also includes an additional ultrasound scanner configured to, as part of the ultrasound examination, generate additional ultrasound data based on reflections of additional ultrasound signals transmitted by the additional ultrasound scanner and communicate wirelessly, over the communication network, the additional ultrasound data to the aggregator. The ultrasound system also includes the aggregator configured to aggregate the ultrasound data and the additional ultrasound data into aggregated ultrasound data and communicate, over the communication network, the aggregated ultrasound data to an archiver for archival into a patient record of the ultrasound examination.

In an example, the communication network includes a wireless access point and the aggregator is implemented to communicate the aggregated ultrasound data to the archiver including to communicate wirelessly the aggregated ultrasound data to the wireless access point. In an embodiment, at least one of the ultrasound data and the additional ultrasound data includes an ultrasound image.

In an embodiment, the ultrasound system includes a display device configured to, as part of the ultrasound examination, display at least one ultrasound image based on at least one of the ultrasound data and the additional ultrasound data. The display device can be implemented to display simultaneously an ultrasound image based on the ultrasound data and an additional ultrasound image based on the additional ultrasound data. In one example, the at least one ultrasound image includes a 3D image. In an embodiment, the at least one ultrasound image includes a four-dimensional (4D) image. In one example, the display device and the aggregator are housed in a common housing.

In an embodiment, the ultrasound scanner is implemented with a first transducer type to generate the ultrasound signals and the additional ultrasound scanner is implemented with a second transducer type to generate the additional ultrasound signals. The ultrasound system can include an ultrasound machine coupled to at least one of the ultrasound scanner and the additional ultrasound scanner and implemented to generate a measurement based on at least one of the ultrasound data and the additional ultrasound data, and communicate the measurement to the aggregator. The aggregator can be implemented to aggregate the measurement with the ultrasound data and the additional ultrasound data into the aggregated ultrasound data. In an example, the measurement includes a caliper distance.

In one embodiment of the present invention an ultrasound system includes a plurality of ultrasound scanners configured to simultaneously scan at least one patient anatomy and generate ultrasound data based on said scan. The ultrasound system also includes a plurality of transceivers coupled to the plurality of ultrasound scanners configured to communicate the ultrasound data to an archiver for aggregation into a patient record.

In one example, the ultrasound system includes a display device. The plurality of ultrasound scanners can be configured to communicate the ultrasound data to the display device over a communication network, and the plurality of transceivers can be configured to communicate the ultrasound data to the archiver using the communication network. The display device can be implemented to simultaneously display a plurality of ultrasound images based on the ultrasound data. In an example, the plurality of ultrasound images includes a first ultrasound image corresponding to a first ultrasound scanner of the plurality of ultrasound scanners and a second ultrasound image corresponding to a second ultrasound scanner of the plurality of ultrasound scanners. In an embodiment, the plurality of ultrasound images includes an additional ultrasound image generated from the ultrasound data corresponding to at least two of the plurality of ultrasound scanners. Additionally or alternatively, the plurality of ultrasound images can include an ultrasound image generated from the ultrasound data corresponding to at least two of the plurality of ultrasound scanners.

In an embodiment, the ultrasound system includes an aggregator implemented to aggregate the ultrasound data for said aggregation into the patient record, and to communicate the ultrasound data to the archiver includes to communicate the ultrasound data to the aggregator. In an example, the aggregator is implemented to communicate the ultrasound data to the archiver.

Embodiments of the ultrasound system for a virtual sonography team described herein can offload the responsibilities of the sonographer, providing better ultrasound examinations and superior patient care than conventional ultrasound systems. The described embodiments provide new ways of viewing the patient's condition in a crowded ER. Multiple staff can have a close-up view of the scans. Staff standing twenty feet away can have a close view. This allows for highly experienced staff to oversee and provide direction for multiple trauma bays, or multiple disciplines to provide input.

The described embodiments allow members of a virtual sonography team to simultaneously save images, annotate images, perform measurements, run AI routines, etc., offloading the sonographer who can concentrate on the patient. Members of virtual sonography team can provide insight to the sonographer from within the care facility during the examination, but out of the way of the patient and staff in the examination room. The virtual sonography team can include staff across multiple disciplines, and their roles can be determined to match their background and training. Use of care-facility network alleviates security issues associated with Internet solutions, and affords routable data in a multicast protocol. With the example of the portable ultrasound scanner, embodiments of the ultrasound system described herein may create a limited distance secure network. The embodiments of the ultrasound system described herein support training of sonography students in a way that reduces the time needed to receive their certifications comparing to conventional ultrasound systems. The embodiments of the ultrasound system described herein improve data collection compared to a single sonographer operating a conventional ultrasound system. This results in better patient care, and improves the manufacturer brand comparing to conventional ultrasound systems.

It is apparent from this description that embodiments described herein may be embodied, at least in part, in software. That is, the techniques and methods may be carried out in a data processing system or set of data processing systems in response to one or more processors executing a sequence of instructions stored in a storage medium, such as a non-transitory machine readable storage media, such as volatile DRAM or nonvolatile flash memory. In various embodiments, hardwired circuitry may be used in combination with software instructions to implement the embodiments described herein. Thus the techniques and methods are not limited to any specific combination of hardware circuitry and software, or to any particular source for the instructions executed by the one or more data processing systems.

In the foregoing specification, specific exemplary embodiments have been described. It will be evident that various modifications may be made to those embodiments without departing from the broader spirit and scope set forth in the following claims. The specification and drawings are, accordingly, to be regarded in an illustrative sense rather than a restrictive sense.

What is claimed is:

1. An ultrasound system comprising:
   an ultrasound scanner configured to, as part of an ultrasound examination administered with the ultrasound system, generate ultrasound data based on reflections of ultrasound signals transmitted by the ultrasound scanner and communicate, over a communication network, the ultrasound data to at least one display device and an archiver;
   an ultrasound machine coupled to the ultrasound scanner and configured to determine examination data for the ultrasound examination and communicate, over the communication network, the examination data to the archiver; and
   the at least one display device coupled to the communication network and configured to generate an ultrasound image based on the ultrasound data as part of the ultrasound examination and communicate the ultrasound image to the archiver for aggregation with the examination data into a patient record of the ultrasound examination, wherein the ultrasound scanner is operated by a first operator and the at least one display device is operated by a first user during the ultrasound examination, and wherein the ultrasound scanner is implemented to receive, via the communication network and from the at least one display device, first user identification data associated with the first user; and communicate to the at least one display device, via the communication network, one or more tasks including a first task to be performed during the ultrasound examination with the at least one display device based on the first user identification data.

2. The ultrasound system as described in claim 1, wherein the ultrasound scanner and the ultrasound machine are located in a first room of a care facility and the at least one display device is located in a second room of the care facility.

3. The ultrasound system as described in claim 1, wherein:
the ultrasound scanner, the ultrasound machine, and the at least one display device are located in a same room of a care facility; and
the ultrasound machine is operated by the first operator during the ultrasound examination.

4. The ultrasound system as described in claim 1, wherein the examination data includes at least one of biometric patient data, patient identification data, an additional ultrasound image, and an imaging parameter.

5. The ultrasound system as described in claim 1, wherein the ultrasound data includes pre-scan-converted image data and the at least one display device is implemented to convert the pre-scan-converted image data into scan-converted image data to generate the ultrasound image.

6. The ultrasound system as described in claim 1, wherein the at least one display device includes a neural network implemented to generate, based on the ultrasound data, at least one of a label, a classification, a segmentation, and a probability; and
the at least one display device is implemented to communicate to the archiver the at least one of the label, the classification, the segmentation, and the probability for said aggregation into the patient record.

7. The ultrasound system as described in claim 1, wherein the one or more tasks include the first task that is determined based on the first user identification data and a second task that is determined based on second user identification data associated with a second user.

8. The ultrasound system as described in claim 7, wherein the ultrasound scanner is implemented to receive, via the communication network and from the at least one display device, operator data including the first user identification data for the at least one display device, and at least one of the ultrasound scanner and the ultrasound machine is implemented to determine the first task based on the first user identification data automatically and without user intervention.

9. The ultrasound system as described in claim 7, wherein at least one of the ultrasound scanner and the ultrasound machine is implemented to receive a user selection that indicates the first task.

10. The ultrasound system as described in claim 1, further comprising an additional ultrasound scanner configured to generate, as part of the ultrasound examination, additional ultrasound data based on additional reflections of additional ultrasound signals transmitted by the additional ultrasound scanner and communicate, over the communication network, the additional ultrasound data to the at least one display device, wherein the at least one display device is configured to:
generate an additional ultrasound image based on the additional ultrasound data;
implement a neural network to generate, based on the ultrasound image and the additional ultrasound image, at least one of a label, a classification, a segmentation, a probability, and a new ultrasound image; and
communicate, over the communication network and to the archiver, the at least one of the label, the classification, the segmentation, the probability, and the new ultrasound image for said aggregation into the patient record.

11. The ultrasound system as described in claim 10, wherein the new ultrasound image includes at least one of a super-resolution image and a three-dimensional image.

12. The ultrasound system as described in claim 1, wherein the ultrasound scanner is patient operated at a first location and the at least one display device is sonographer operated at a second location that is different from the first location.

13. An ultrasound system comprising:
an ultrasound scanner configured to, as part of an ultrasound examination administered with the ultrasound system, generate ultrasound data based on reflections of ultrasound signals transmitted by the ultrasound scanner and communicate, over a communication network, the ultrasound data to a display device and an archiver; and
the display device coupled to the communication network and configured to generate, with a neural network implemented at least partially in hardware of the display device, an inference based on the ultrasound data and communicate the inference, over the communication network, to the archiver for aggregation with the ultrasound data into a patient record of the ultrasound examination, wherein the ultrasound scanner is operated by a first operator and the display device is operated by a first user during the ultrasound examination, wherein the ultrasound scanner is configured to:
receive, via the communication network and from the display device, first user identification data associated with the first user;
obtain a first task to be performed for the ultrasound examination based on the first user identification data; and communicate, via the communication network and to the display device, the first task.

14. The ultrasound system as described in claim 13, wherein the display device includes a server device.

15. The ultrasound system as described in claim 13, further comprising the archiver configured to communicate, over the communication network, the patient record to a database of a care facility where the ultrasound examination is performed.

16. The ultrasound system as described in claim 13, wherein the display device is configured to generate an ultrasound image based on the ultrasound data and display the ultrasound image.

17. The ultrasound system as described in claim 13, wherein:
the ultrasound scanner is configured to:
receive, from the display device, operator data including second user identification data associated with a second user of the display device;
obtain a second task for the ultrasound examination based on the second user identification data; and communicate, to the display device, the second task; and
the display device is configured to select the neural network from a plurality of neural networks based on the first task or the second task.

18. The ultrasound system as described in claim 13, wherein the display device is configured to determine the operator data including the first user identification data for a first user of the display device and select the neural network from a plurality of neural networks based on the first user identification data.

19. A method implemented by an ultrasound system comprising an ultrasound scanner and one or more display devices that are wirelessly coupled to the ultrasound scanner via a communication network to perform an ultrasound examination, the method comprising:
- receiving, by the ultrasound scanner via the communication network, first user identification data associated with a first user;
- wirelessly communicating, by the ultrasound scanner, one or more tasks of the ultrasound examination to one or more display devices via the communication network, wherein the ultrasound scanner is operated by a first operator and the one or more display devices include a first display device that is operated by the first user during the ultrasound examination, and wherein the one or more tasks include a first task to be performed by the first display device during the ultrasound examination that is determined based on the first user identification data;
- transmitting, by the ultrasound scanner and over the communication network, ultrasound imaging data to the one or more display devices;
- generating, by the one or more display devices, ultrasound examination data based on the ultrasound imaging data and the one or more tasks; and
- instructing, by the one or more display devices, an archiver to aggregate the ultrasound examination data from the one or more display devices into a patient record of the ultrasound examination.

20. The method as described in claim 19, wherein the one or more tasks include the first task of generating an ultrasound image with a first display device of the one or more display devices and a second task of generating a neural network inference with a second display device of the one or more display devices that is determined based on second user identification data, and the ultrasound examination data aggregated into the patient record includes the ultrasound image and the neural network inference.

21. The method as described in claim 19, wherein the ultrasound imaging data includes ultrasound images and the one or more tasks include the first task of generating annotations for the ultrasound images as part of the ultrasound examination data and a second task of selecting one or more images from the ultrasound images to include in the ultrasound examination data and aggregate into the patient record that is determined based on second user identification data.

* * * * *